United States Patent
Iseberg et al.

(10) Patent No.: US 10,085,677 B2
(45) Date of Patent: Oct. 2, 2018

(54) SYSTEM AND METHOD FOR PERFORMING A HEARING SCREENING

(75) Inventors: Steve Iseberg, Palatine, IL (US); Steve Viranyi, Palatine, IL (US); Gregory R. Shaw, Calgary (CA); Viorel Drambarean, Skokie, IL (US); John Stuhr French, Arlington Heights, IL (US); Ron Scicluna, Hampshire, IL (US); Mead C. Killion, Elk Grove Village, IL (US)

(73) Assignee: ETYMOTIC RESEARCH, INC., Elk Grove Village, IL (US)

( * ) Notice: Subject to any disclaimer, the term of this patent is extended or adjusted under 35 U.S.C. 154(b) by 3334 days.

(21) Appl. No.: 11/280,873

(22) Filed: Nov. 16, 2005

(65) Prior Publication Data

US 2007/0112279 A1    May 17, 2007

(51) Int. Cl.
| | | |
|---|---|---|
| A61B 5/12 | (2006.01) | |
| A61B 5/03 | (2006.01) | |
| A61B 5/00 | (2006.01) | |
| A61B 1/227 | (2006.01) | |

(52) U.S. Cl.
CPC .............. *A61B 5/121* (2013.01); *A61B 5/03* (2013.01); *A61B 5/125* (2013.01); *A61B 5/126* (2013.01); *A61B 5/6817* (2013.01); *A61B 1/2275* (2013.01)

(58) Field of Classification Search
CPC ........... A61B 5/12; A61B 5/121; A61B 5/125; A61B 5/126; A61B 5/128; A61B 5/048045; A61B 5/6817; A61B 5/123
USPC ............... 600/559, 561, 544, 372, 379, 587; 73/585; 601/76; 181/126
See application file for complete search history.

(56) References Cited

U.S. PATENT DOCUMENTS

| | | | | |
|---|---|---|---|---|
| 3,882,848 A | * | 5/1975 | Klar et al. | 600/559 |
| 3,954,351 A | * | 5/1976 | Scholl et al. | 417/40 |
| 4,002,161 A | * | 1/1977 | Klar et al. | 600/559 |
| 4,237,905 A | * | 12/1980 | Keller | A61B 5/12 |
| | | | | 600/559 |
| 4,681,242 A | * | 7/1987 | Sirkin | 222/41 |
| 4,688,582 A | | 8/1987 | Heller | |
| 5,105,822 A | * | 4/1992 | Stevens et al. | 600/559 |
| 5,601,091 A | | 2/1997 | Dolphin | |
| 5,792,073 A | * | 8/1998 | Keefe | 600/559 |
| 5,857,775 A | * | 1/1999 | Vodzak et al. | 374/131 |

(Continued)

FOREIGN PATENT DOCUMENTS

| | | |
|---|---|---|
| WO | WO 00/65983 | 11/2000 |
| WO | WO03058067 A1 | 7/2003 |

OTHER PUBLICATIONS

International Search Report for PCT/US2006/035964 dated Mar. 20, 2007.

(Continued)

*Primary Examiner* — Adam J Eiseman
(74) *Attorney, Agent, or Firm* — McAndrews, Held & Malloy, Ltd.

(57) ABSTRACT

A hearing screening system for testing hearing abilities of a patient includes an otoacoustic emission (OAE) module operable to perform OAE tests, a tympanometry (tymp) module operable to perform tymp tests, and at least one probe in communication with at least one of the OAE and tymp modules. The probe includes a probe tip that is configured to be positioned within an ear canal of a patient.

18 Claims, 14 Drawing Sheets

(56) References Cited

U.S. PATENT DOCUMENTS

| | | | |
|---|---|---|---|
| 6,137,889 A * | 10/2000 | Shennib et al. | 381/328 |
| 6,149,605 A * | 11/2000 | Christiansen | 600/559 |
| 6,167,138 A | 12/2000 | Shennib | |
| 6,231,521 B1 | 5/2001 | Zoth | |
| 6,496,585 B1 | 12/2002 | Margolis | |
| 6,974,421 B1 * | 12/2005 | Causevic et al. | 600/561 |
| 7,200,760 B2 * | 4/2007 | Riebe et al. | 713/194 |
| 7,268,466 B2 * | 9/2007 | Rasmussen | 310/328 |
| 2004/0071295 A1 * | 4/2004 | Wasden et al. | 381/60 |
| 2004/0152998 A1 * | 8/2004 | Stott et al. | 600/559 |
| 2005/0015018 A1 | 1/2005 | Dolphin | |

OTHER PUBLICATIONS

American Speech Language Hearing Association Audiologic Assessment Panel 1996, Guidelines for Audiologic Screening (1997).

"Classroom Management of Children With Minimal Hearing Loss," Flexer, C., Hearing Journal, vol. 48(9), pp. 54-58 (1995).

"Outcomes of Transient Evoked Otoacoustic Emission Testing in 6-Year Old School Children: A Comparison With Pure Tone Screening and Tympanometry," Driscoll, C., Kei, J., & McPherson, B. Int. J. Pediatr. Otorhinolaryngol, vol. 57(1), pp. 67-76 (2001).

"Distortion Product Otoacoustic Emissions in Children at School Entry: A Comparison With Pure-Tone Screening and Tympanometry Results," Lyons, A., Kei, J., & Driscoll, C., J. Am. Acad. of Audiology, vol. 15(10), pp. 702-15 (2004).

"Screening for Hearing Loss and Middle-Ear Disorders in Children Using TEOAEs," Taylor, C., & Brooks R., American Journal of Audiology, vol. 9(1), pp. 50-55 (2000).

ERo-SCAN OAE Test System product brochure (May 2004).

Operating INstructions for ERO-SCAN OAE Test System (2003).

Capella Otoacoustic Emissions System product brochure (Madsen) (Jan. 2004).

"Build your own Windows-based syetm for objection diagnostics" (Madsen) (Jan. 2004).

Chinese Patent Office, Second Office Action dated Apr. 28, 2010, in Chinese patent application No. 200680043063.9.

EPO Communication dated Jun. 30, 2011 in Application No. 06 803 655.7—1526 (5 pages).

Canadian communication dated Jul. 6, 2011 in Application No. 2,623,598 (3 pages).

Chinese Patent Office, The First Office Action in Application No. 201010288472.3, dated Mar. 29, 2011.

* cited by examiner

SYSTEM AND METHOD FOR PERFORMING A HEARING SCREENING

BACKGROUND OF THE INVENTION

Embodiments of the present invention generally relate to a system and method for performing a hearing screening, and more particularly, to a system and method for performing a hearing screening using a plurality of audiometric evaluations and measurements.

Typical audiometric evaluations and hearing screenings include several measurements used either in isolation or in combination. The measurements include acoustic measures, such as tympanometry and acoustic reflexes; evoked responses, such as otoacoustic emission measures and auditory brainstem response; and behavioral responses, such as pure-tone testing.

With respect to tympanometry, a probe having an eartip is placed in the opening of the ear canal. The eartip sealingly engages the opening of the ear canal. A probe tone (for example, 226 Hz or 1 kHz) is transmitted within the ear canal, while the air pressure in the ear canal is varied from positive to negative within a specified range (for example, +200 to −400 daPa). Reflected sound from the tympanic membrane is used to determine the middle ear pressure, that is, peak compliance, and mobility of the system, that is, static compliance. The peak compliance and static compliance reflect the status and function of the tympanic membrane, ossicles, middle ear space and Eustachian tube, thereby providing an objective measure of the auditory periphery to the point of the middle ear.

As noted above, tympanometry utilizes pressure fluctuations within the ear canal. Typical tympanometry devices include a continuous pump used to produce pressure differentials within the sealed ear canal (that is, the eartip of the probe sealingly engages the opening of the ear canal). Continuous pumps, however, may produce pressures that may damage anatomical structures within the ear. In short, the continuous pumps do not have limit stops or other features that limit levels of imparted pressure. For example, a continuous pump may be continually operated to produce a positive pressure. If left unchecked, however, the resulting pressure may exceed the threshold of pain for a particular individual. In short, there is no inherent limit to the amount of pressure that may be generated with respect to tympanometry systems that include continuous pumps. Also, typical tympanometry systems are large and bulky due, in part, to the continuous pumps contained therein. For example, the continuous pumps typically include large motors connected to a peristaltic pump, thereby adding size and bulk to the tympanometry system.

Otoacoustic emissions (OAEs) represent another hearing test, and are a direct measure of cochlear status as represented by outer hair cell function. The cochlea is the sensory organ of hearing responsible for transmitting acoustic information to the auditory nerve. The outer hair cells of the cochlea play a critical role with respect to processes within the cochlea. In a normal cochlea, the outer hair cells are involved in an active process known as the cochlear amplifier. As a byproduct of their active processes, the outer hair cells produce a low level sound that may be measured in the ear canal with a sensitive low-noise microphone. The low level sound is known as the otoacoustic emission. In the presence of sensory hearing loss, an otoacoustic emission is absent or significantly reduced in amplitude. Otoacoustic emissions are classified by the type of stimulus used to evoke the response from the outer hair cells. Transient evoked otoacoustic emissions (TEOAEs) are emitted in response to a short duration stimulus such as a click. Distortion product otoacoustic emissions (DPOAEs) are emitted in response to a simultaneous presentation of two pure tones of differing frequencies. TEOAEs and DPOAEs represent the two most common types of clinical otoacoustic emission measurements. Otoacoustic emission measurements are used to assess the function of the auditory periphery to the point of the cochlea, specifically the outer hair cells of the cochlea.

Acoustic reflex (AR) is a measurement of the contraction of the stapedius muscle in response to a high intensity stimulus. In acoustic reflex testing, air pressure within the ear canal is maintained at the point of peak compliance while tones of various intensities and/or frequencies are presented. Contraction of the stapedius muscle in response to a loud sound stiffens the conductive mechanism, causing a change in middle ear immittance, which may be detected. The acoustic reflex arc involves the cochlea, cranial nerve VIII (auditory nerve), ventral cochlear nucleus, superior olivary complex, facial nerve nucleus, cranial nerve VII (facial nerve), and the stapedius muscle. As such, an acoustic reflex measure is used to assess auditory pathways to the point of the superior olivary complex of the brainstem.

Auditory brainstem response (ABR) is an evoked potential in response to a brief click or tone-burst stimulus delivered to the ear via an earphone. The response waveform is measured with electrodes placed on the scalp and earlobes. Evaluation of the resulting waveform provides an assessment of the auditory system to the point of the inferior colliculus of the brainstem (one level above the superior olivary complex).

A strong commitment to the prevention, early detection and treatment of hearing loss and otologic disorders exists within the audiology, education, and medical communities. To that end, screening measures are used to identify those individuals who may, upon complete evaluation, demonstrate a hearing loss or pathology requiring remediation or medical treatment. The emphasis on early detection of hearing loss stems from the desire to begin audiological and/or medical intervention as soon as possible. The presence of childhood hearing loss is known to interfere with the development of speech and language skills. According to the American Speech-Language-Hearing Association (ASHA), "Hearing impairment adversely affects the developing auditory nervous system and can have harmful effects on social, emotional, cognitive, and academic development, and, subsequently, on the individual's vocational and economic potential." See American Speech Language Hearing Association Audiologic Assessment Panel 1996, *Guidelines For Audiologic Screening* (1997). The probability of preventing permanent development delays increases the earlier a hearing impairment is identified and treatment begins. See id. It is with this knowledge that ASHA audiologic screening guidelines recommend regular screening for hearing disorder and hearing impairment for children age birth to eighteen years. See id.

Available screening procedures include otoscopic evaluation, tympanometry, otoacoustic emission (OAE) measurements, auditory brainstem response (ABR), and pure-tone testing. Each of these measures assesses the auditory system to a certain anatomical point. Otoscopy allows for visual evaluation of the external ear canal and tympanic membrane. Tympanometry assesses the function of the middle ear system (tympanic membrane and ossicles). OAEs are a direct and objective measure of the outer hair cells of the cochlea (sensory) and the ABR assesses the auditory system to the point of the brainstem (neural). Finally, in pure-tone testing a tone is delivered to the patient and a response is required from the patient thereby evaluating the auditory system to a cortical level. OAE testing is the newest measurement type of those described, having entered the clinical arena in the early 1990's. In the last decade, OAEs have gained nearly unanimous acceptance as a means of screening for sensory hearing loss, the most common type of permanent hearing loss. OAEs are particularly useful for screening newborns, infants, and children as no response is required from the patient. As part of the diagnostic audiology test battery, OAE measurements are conducted on patients of all ages.

According to ASHA screening guidelines, "Ideally a screening test should be easy to administer, comfortable for the patient, short in duration, and inexpensive." See American Speech Language Hearing Association Audiologic Assessment Panel 1996, *Guidelines For Audiologic Screening* (1997). An objective measure is particularly desirable when testing young children or other difficult-to-test populations and when the tester has no particular education and/or expertise related to audiometric evaluations. Additionally, the test should be able to separate those with hearing loss from those without hearing loss via a "pass" or "refer" outcome. No test can offer 100% specificity and sensitivity but it is important to avoid a high over-referral rate due to the burden it places on follow-up resources. On the other hand, a high under-referral rate must also be avoided. Failure to identify individuals with hearing loss results in delayed treatment and ultimately a loss of faith in the screening program.

Often, emphasis is placed on identifying only sensory or neural hearing losses. This focus is most likely due to the often severe and permanent nature of sensory-neural hearing loss. Equally important, however, is the ability to detect middle ear pathology such as chronic otitis media with effusion and related conductive hearing loss. Within the pediatric population there is a high prevalence of middle ear pathology that is known to have both medical and developmental consequences. See, e.g., American Speech Language Hearing Association Audiologic Assessment Panel 1996, *Guidelines For Audiologic Screening* (1997), and, "Classroom Management Of Children With Minimal Hearing Loss," Flexer, C., *Hearing Journal*, Volume 48(9), pp. 54-58 (1995).

In screening for sensory hearing losses in the school-age population, testing is commonly conducted with OAE or pure-tone testing. The decision to use one method over another will depend on the age of the patient, assessment of risk factors and patient history, skill level and training of the tester, available equipment, protocol of the screening program and a myriad of other factors. There are advantages, disadvantages and limitations to each type of test. In screening for middle ear pathology, some authorities support the use of tympanometry combined with a second measure such as pure-tone or OAE testing. See, e.g., "Outcomes Of Transient Evoked Otoacoustic Emission Testing In 6-Year Old School Children: A Comparison With Pure Tone Screening And Tympanometry," Driscoll, C., Kei, J., & McPherson, B. *Int. J. Pediatr. Otorhinolaryngol*, Volume 57(1), pp. 67-76 (2001); "Distortion Product Otoacoustic Emissions In Children At School Entry: A Comparison With Pure-Tone Screening And Tympanometry Results," Lyons, A., Kei, J., & Driscoll, C., *J. Am. Acad. Of Audiology*, Volume 15(10), pp. 702-15 (2004); and "Screening For Hearing Loss And Middle-Ear Disorders In Children Using TEOAEs," Taylor, C., & Brooks R., *American Journal Of Audiology*, Volume 9(1), pp. 50-55 (2000). Therefore, if detection of middle ear pathology is included as an objective of the screening program, the protocol will likely include tympanometry.

As noted above, an effective screening program should aim for low rate of over-referrals (that is, false-positives) and under-referrals (that is, false-negatives or misses). While some authorities support the replacement of pure-tone screening with OAE testing based on sensitivity and specificity data, neither OAE nor pure-tone testing is a suitable replacement for tympanometry. See, e.g., "Outcomes Of Transient Evoked Otoacoustic Emission Testing In 6-Year Old School Children: A Comparison With Pure Tone Screening And Tympanometry," Driscoll, C., Kei, J., & McPherson, B. *Int. J. Pediatr. Otorhinolaryngol*, Volume 57(1), pp. 67-76 (2001); and "Screening For Hearing Loss And Middle-Ear Disorders In Children Using TEOAEs," Taylor, C., & Brooks R., *American Journal Of Audiology*, Volume 9(1), pp. 50-55 (2000). Additionally, OAEs typically provide a much shorter test time, as compared to pure-tone testing, particularly with respect to the younger range of the pediatric population.

In any event, in order to perform various screening tests, various testing systems are used. For example, if OAE testing and tympanometry testing are to be performed, a screener typically uses an OAE system and a separate and distinct tympanometry system that may be large and bulky. The screening process using these tests takes time because the screener typically changes screening hardware between tests. For example, the OAE system includes its own probe, while the tympanometry system includes a separate and distinct probe. As such, the screener must switch probes between tests.

Thus, a need exists for a safe, compact system and method for performing OAE and tympanometry screening. Additionally, a need exists for quickly and effectively performing a variety of hearing tests.

SUMMARY OF THE INVENTION

Certain embodiments of the present invention provide a hearing screening system for testing hearing abilities of a patient. The system includes an otoacoustic emission (OAE) module operable to perform OAE tests, a tympanometry (tymp) module operable to perform tymp tests, and at least one probe in communication with at least one of the OAE module and the tymp module. The probe includes a probe tip that is configured to sealingly engage an opening of an ear canal of the patient.

The OAE module may be a handheld device, and the tymp module may include a separate housing connected to the handheld device. Optionally, the OAE module and the tymp module may be contained within a single housing, such as a handheld device.

The tymp module may include at least one sound receiver in communication with the probe, a pressure sensor in communication with the probe, and a pump subsystem connected to the probe through an air tube. The pump subsystem is operable to vary air pressure proximate the probe when the probe tip is inserted into an ear canal of a patient. That is, the pump subsystem is operable to vary air pressure within the ear canal of the patient when the probe tip is positioned within the ear canal. The pump subsystem may be a fixed displacement pump subsystem that limits applied maximum and minimum air pressure.

The pump subsystem may include a pump cylinder in fluid communication with the air tube, a piston slidably retained within the pump cylinder, a link pivotally connected to the pump cylinder, and a lever arm supporting the link. Radial motion of the lever arm is translated into linear motion of the piston within the pump cylinder through the link. The system may also include first and second limit switches operable to detect a position of the lever arm.

The system may also include a motor operatively connected to a drive shaft that engages the lever arm. The motor operates to rotate the drive shaft, such that the rotation of the drive shaft causes the lever arm to radially move. The drive shaft may be threaded from a first location to a second location. The drive shaft threadably engages the lever arm, wherein movement of the lever arm on the drive shaft is limited between movement from the first location to the second location.

The system may also include a user interface and a memory that stores a plurality of activation codes corresponding to pre-paid hearing tests. A test procedure is activated when a unique code input at the user interface matches one of the plurality of activation codes.

The probe may include a rear housing, a probe tip, a probe head, a microphone, and a first sound receiver. The probe tip is configured to removably secure to the rear housing. The probe head may be securely retained within at least one of the rear housing and the probe tip. The probe head may include a microphone port, a first sound receiver port and a second sound receiver port. The microphone may be secured within the probe head proximate the microphone port. The first sound receiver may also be secured within the probe head, wherein the first sound receiver couples to the first sound receiver port through a first sound tube.

The probe may also include an air tube disposed within at least one of the rear housing and the probe tip housing. Additionally, the probe may include a pressure sensor tube disposed within at least one of the rear housing and the probe tip housing.

The probe may also include a second sound tube connected to the second sound receiver port, wherein at least one of the first and second sound tubes exhibits a high acoustic impedance. An inner diameter of the first sound tube may differ from an inner diameter of the second sound tube.

Certain embodiments of the present invention also provide a method of calibrating a tympanometry (tymp) module. The method includes detecting first and second motion limits of a lever arm connected to a piston that is slidably secured within a pump cylinder, correlating the first and second motion limits of the lever arm with motion of the piston within the pump cylinder, determining a motion characteristic from the detecting step, determining a center position of the lever arm and the piston from the determining a motion characteristic step, and positioning the lever arm and the piston at the center position. The center position may correspond to ambient air pressure. Moving the lever arm in a first direction from the center position may cause the piston to push air out of the pump cylinder, and moving the lever arm in a second direction from the center position may cause the piston to draw air into the pump cylinder. The motion characteristic may be elapsed time between movement of the lever arm from the first motion limit to the second motion limit, or the distance traveled by the lever arm from the first motion limit to the second motion limit.

Figure 1:
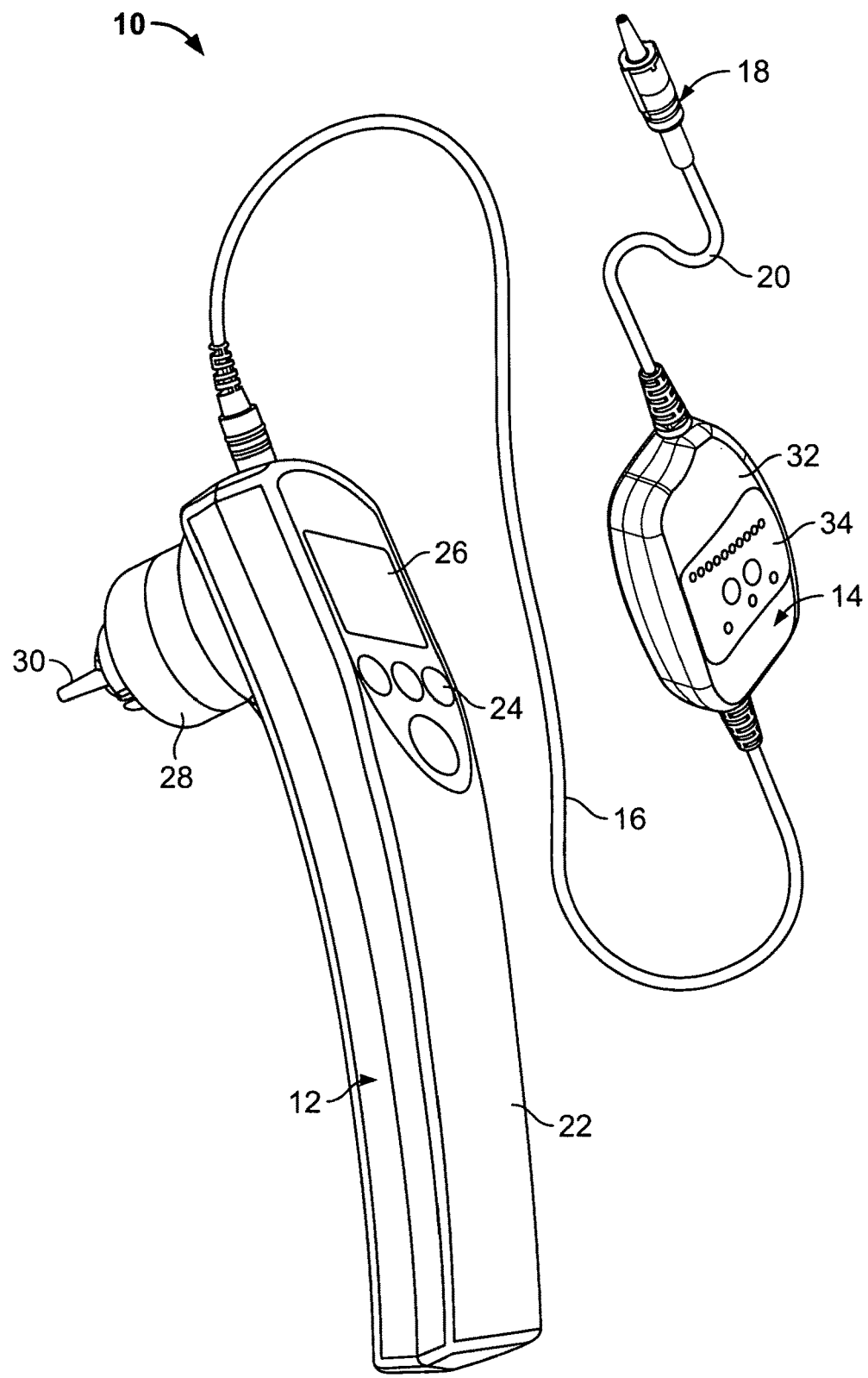
FIG. 1 illustrates an isometric view of a hearing screening system according to an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION OF THE INVENTION

FIG. 1 illustrates an isometric view of a hearing screening system 10 according to an embodiment of the present invention. The hearing screening system 10 includes an otoacoustic emission (OAE) unit or module 12 connected to a tympanometry (tymp) unit or module 14 through a connection 16. The tymp module 14 is, in turn, connected to a remote probe 18 through a connection 20. The connections 16 and 20 may be cables that secure and protect various electrical wires, air tubes, sound tubes, sensor tubes, and the like.

The OAE module 12 includes a main body 22 having a keypad 24 and display 26. A probe 28 extends outwardly from the main body 22 and includes a probe tip 30 that is configured to be positioned within an ear canal opening of a patient. The OAE module 12 may be a hand held device designed to provide an objective measure of outer hair cell function through the measurement of cochlear emissions, such as the Etymotic Research Otoacoustic Emissions Scanner ("ERO-SCAN") OAE Test System, manufactured for Maico Diagnostics of Eden Prairie, Minnesota. The OAE module 12 is operable to perform known OAE tests and procedures.

The tymp module 14 includes a main housing 32 having an operation interface 34. The tymp module 14 is operable to perform tympanometry tests and procedures. While the tymp module 14 is shown connected to the OAE module 12 and the probe 18 through connections 16 and 20, respectively, the tymp module 14 and the OAE module 12 may be integrated into a single housing. For example, the tymp module 14 may be housed within the main body 22 of the OAE module 12.

Figure 2:
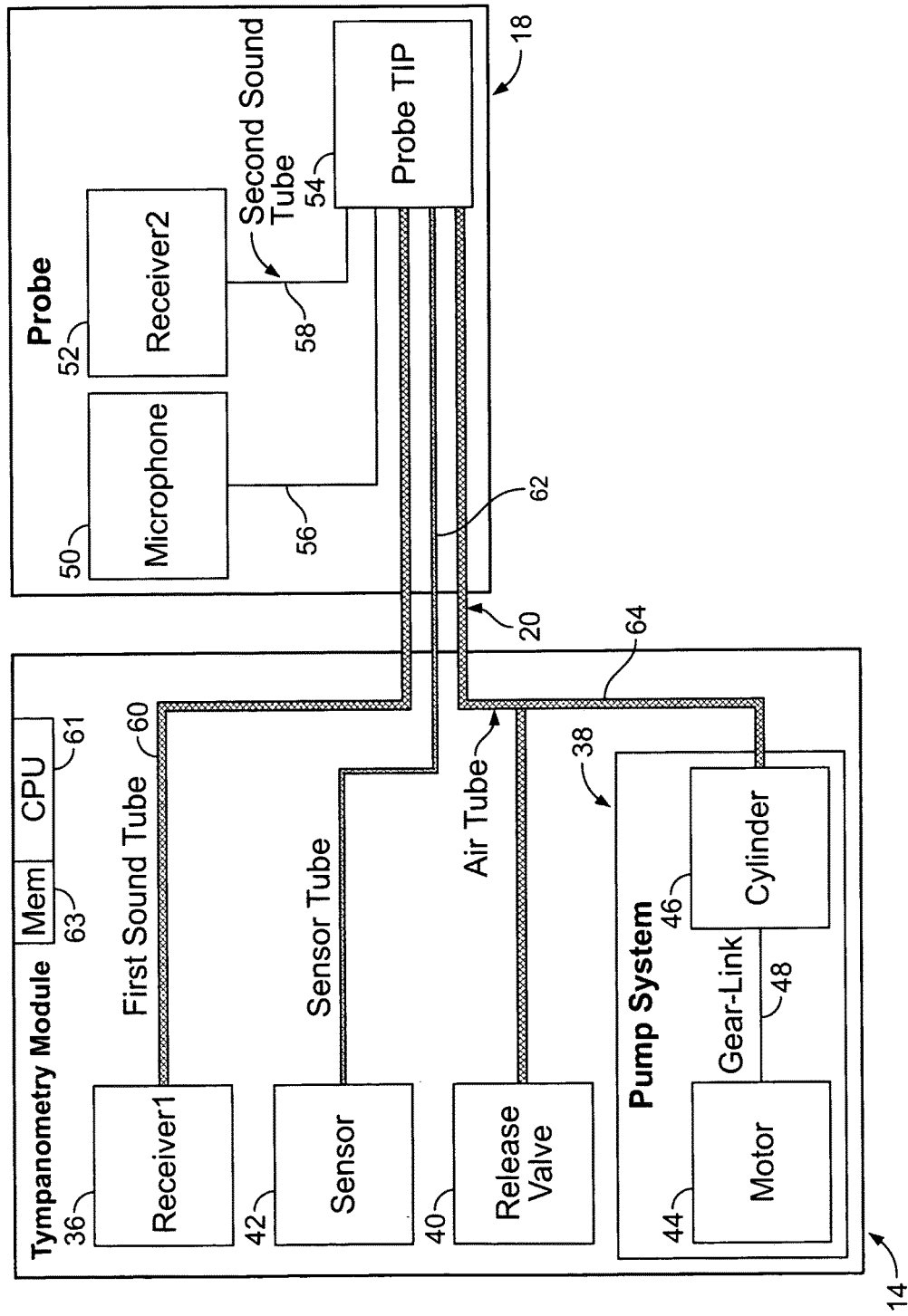
FIG. 2 illustrates a block diagram of a tympanometry module and probe according to an embodiment of the present invention.

FIG. 2 illustrates a block diagram of the tymp module 14 and the probe 18. The tymp module 14 includes a first sound receiver 36, a pump system 38, a pressure release valve 40, and a pressure sensor 42. The pump system 38 includes a motor 44 operatively connected to a pump cylinder 46 through a mechanical link 48. The probe 18 includes a microphone 50 and a second sound receiver 52 in communication with a probe tip 54 through a microphone sound tube 56 and a second receiver sound tube 58, respectively.

The first sound receiver 36 may be connected to the probe tip 54 through a first sound tube 60, which may pass, or be connected to other tubing, through the tymp module 14 and into the probe 18 through the connection 20. The first sound receiver 36 is configured to source sounds that pass through the sound tube 60 into the probe tip 54. The first sound receiver 36 is configured to receive sounds that pass through the probe tip 54 and into the sound tube 60. The receiver 36 is also in communication with a central processing unit (CPU) 61, including a memory 63, that may be positioned within the tymp module 14, as shown in FIG. 2, or the OAE module 12. The processing unit 61 is in communication with the first sound receiver 36, the sensor 42, the pressure release valve 40, the pump system 38, and the microphone 50 and the second sound receiver 52. Alternatively, the first sound receiver 36 and the sound tube 60 may be housed within the probe 18.

The pressure sensor 42 is connected to the probe tip 54 through a sensor tube 62, which passes through the connection 20 into the probe 18. The pressure sensor 42 is also connected to the processing unit 61 and is configured to detect the air pressure at the probe tip 54. To that end, the sensor tube 62 is a relatively small diameter tube having a relatively high acoustic impedance in order to avoid lags in receiving a pressure signal from the probe tip 54. For example, the inner diameter of the sensor tube 62 may be less than ⅓ mm). Additionally, because the sensor tube 62 has a relatively high acoustic impedance, audio interference from sound channels within the probe 18 is minimized. That is, because the sensor tube 62 has a relatively small diameter (and therefore a high acoustic impedance), it is less likely that extraneous outside sounds will pass into the sensor tube 62. Alternatively, the pressure sensor 42 and the sensor tube 62 may be housed within the probe 18.

The pump system 38 is connected to the probe tip 54 through an air tube 64, which passes into the probe 18 through the connection 20. The air tube 64 is relatively large to minimize time delay in delivering a change in air pressure from the pump to the probe 18. The pump system 38 is configured to create negative and positive pressures within an ear canal sealed by the probe tip 54, which includes air passages for air to pass. The release valve 40 is disposed within the air tube 64 between the probe tip 54 and the pump system 38. The release valve 40 may be automatically or manually activated to release air pressure within the tube 64, and therefore an ear canal sealed by the probe tip 54, which is in fluid communication with the air tube 64. The pump system 38 is also connected to the processing unit 61, which operates and controls the pump system 38 based on information received from the pressure sensor 42.

The microphone 50 within the probe 18 is configured to receive or sense sounds, such as clicks or tones, in the probe tip 54 through the sound tube 56. The microphone 50 may be controlled through the processing unit 61. The second sound receiver 52 is configured to transmit sounds through the sound tube 58 to the probe tip 54. The second sound receive 52 may also be controlled through the processing unit 61. Sounds received by the microphone 50 and/or the second sound receiver 52 are relayed to the processing unit 61 for analysis. Alternatively, the microphone 50 and the second sound receiver 52 may be housed within the tymp module 14.

As shown in FIG. 2, the diameter of the sound tubes 56 and 58 is relatively small. For example, the inner diameters of the sound tube 56 and 58 may be less than ¼ mm. As such, the sound tubes 56 and 58 have a relatively high acoustic impedance, thereby minimizing interference between the two sound tubes 56 and 58. Also, the sound tubes 56 and 58 have smaller diameters, and therefore, higher acoustic impedances, than the pressure sensor tube 62. The pressure sensor tube 62 has a smaller diameter, and therefore a higher acoustic impedance, than the sound tubes 60 and 64. Alternatively, the sound tubes 56, 58, 60, the air tube 64, and the pressure sensor tube 62 may be sized differently. For example, the inner diameter of the sound tube 58 may be smaller than the inner diameter of the sound tube 56, or vice versa.

Figure 3:
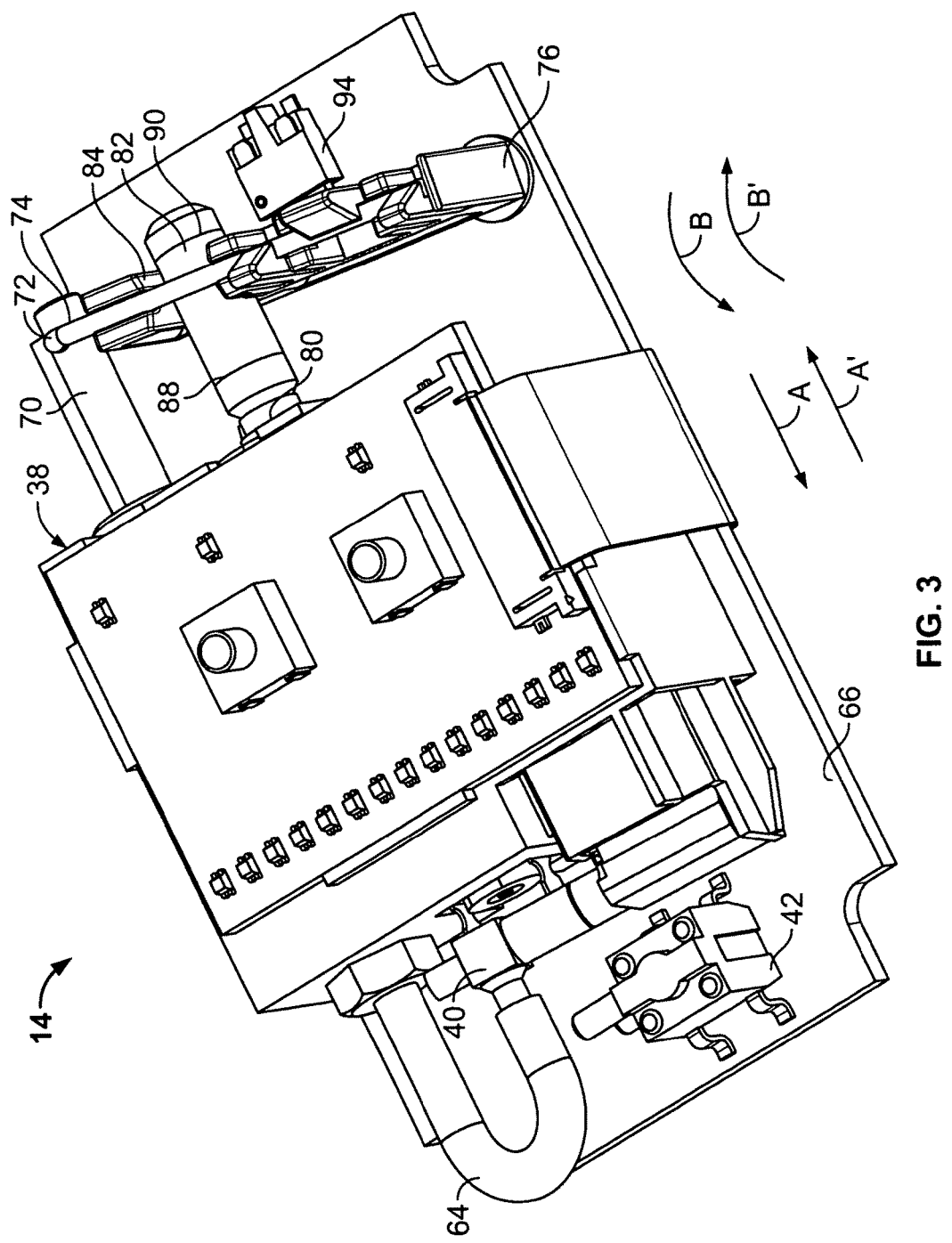
FIG. 3 illustrates a top isometric view of a tympanometry module from a first end according to an embodiment of the present invention.
Figure 4:
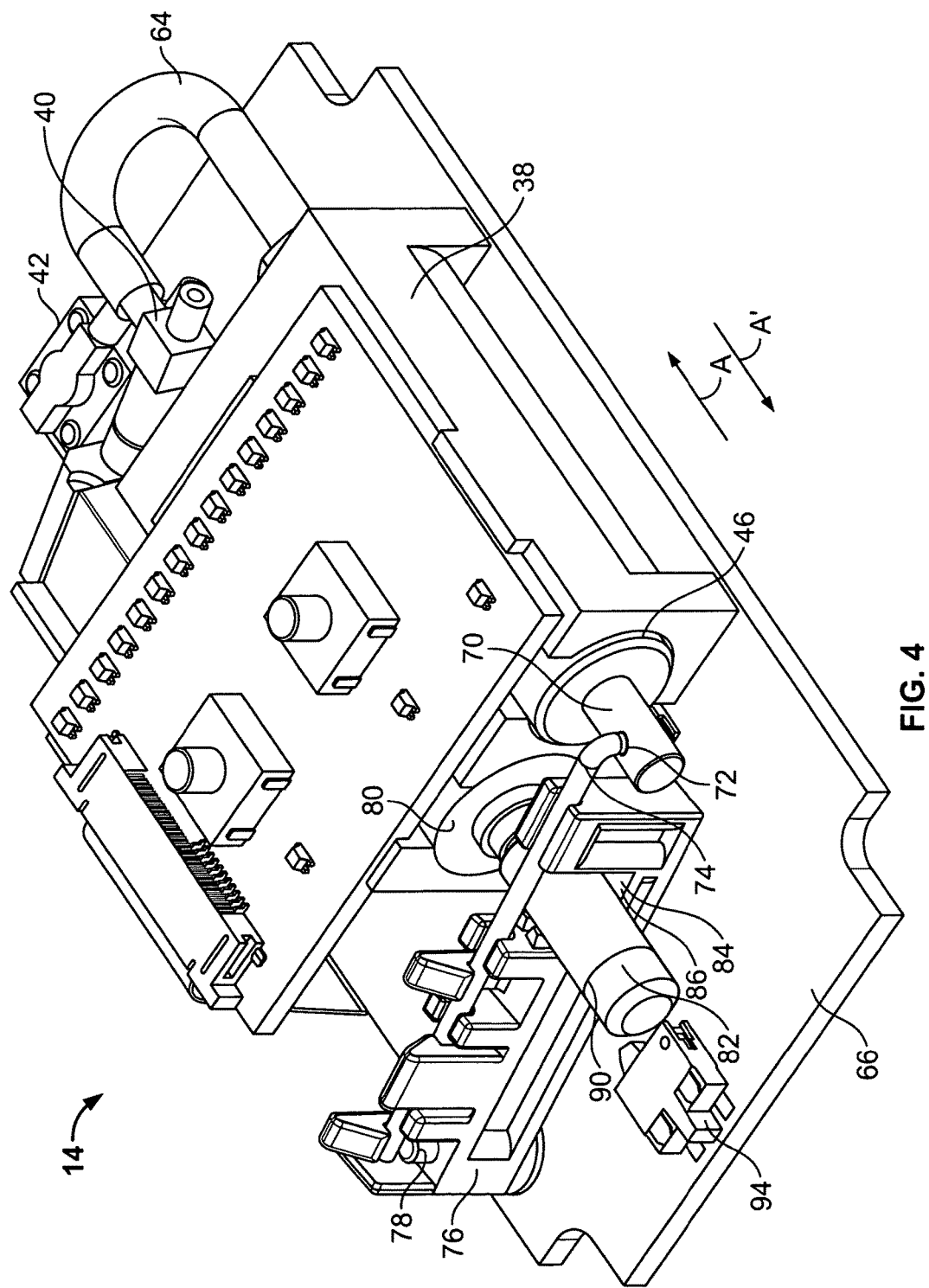
FIG. 4 illustrates a top isometric view of a tympanometry module from a second end according to an embodiment of the present invention.
Figure 5:
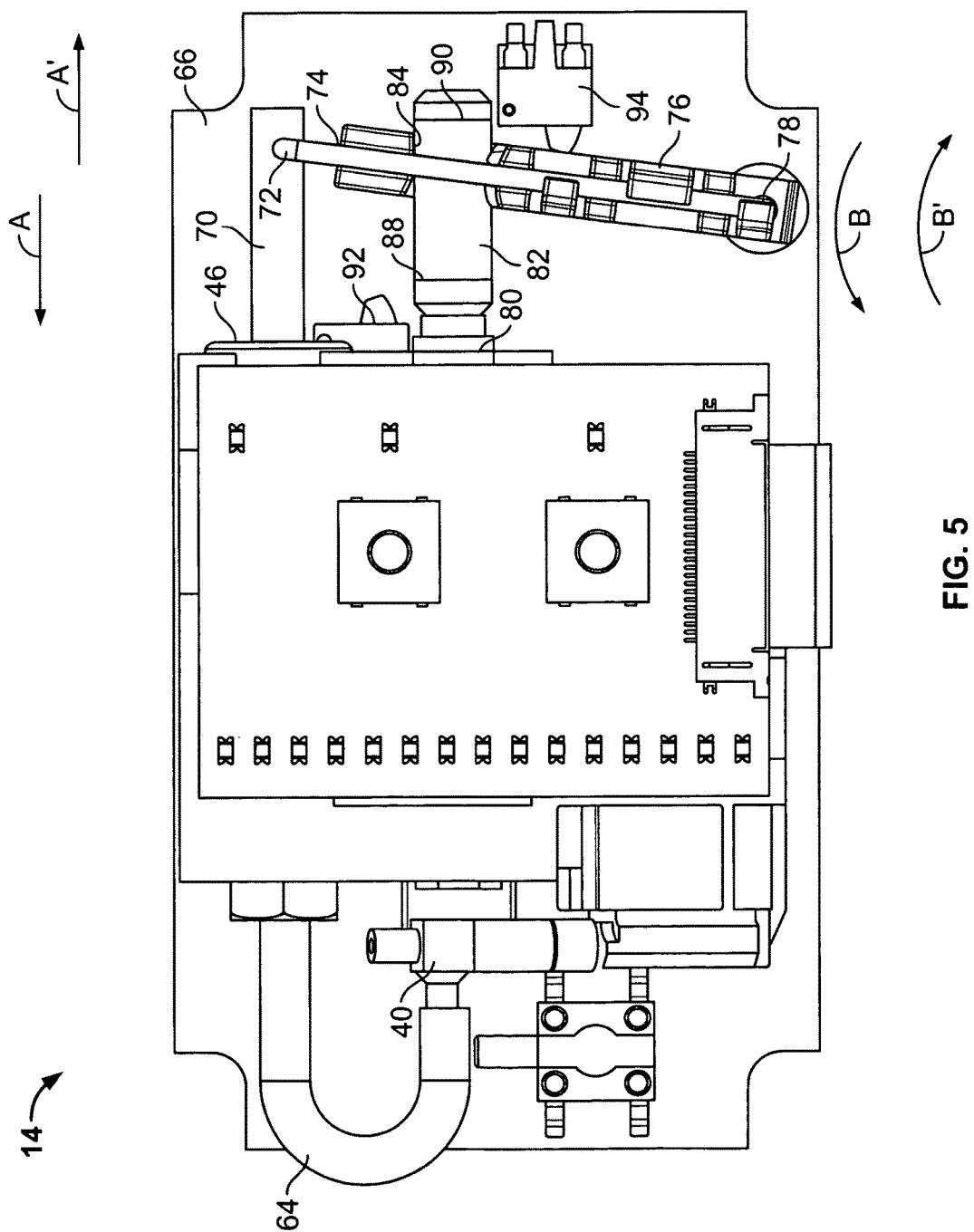
FIG. 5 illustrates a top plan view of a tympanometry module according to an embodiment of the present invention.

FIGS. 3 and 4 illustrate a top isometric view of the tymp module 14 from first and second ends. FIG. 5 illustrates a top plan view of the tymp module 14. In order to show the internal components of the tymp module 14, FIGS. 3-5 show the tymp module 14 without the main housing 32 (shown in FIG. 1). Referring to FIGS. 3-5, the tymp module 14 includes a base 66 that supports and retains the pump system 38, the pressure sensor 42, and various other components of the tymp module 14. The base 66 may be, or may include, a printed circuit board that includes the processing unit 61 (shown in FIG. 2).

The pump system 38 includes the sealed pumping cylinder 46 having a piston 70 slidably disposed therein. The sealed pumping cylinder 46 is in fluid communication with the air tube 64. Movement of the piston 70 within the cylinder 46 causes pressure differentials within the air tube 64. For example, movement of the piston 70 into the cylinder 46 forces air within the cylinder 46 into the air tube 64, and consequently the probe 18 (shown in FIG. 2), thereby increasing air pressure at the probe tip 54 (shown in FIG. 2) when the probe tip 54 sealingly engages an opening of an ear canal. Conversely, movement of the piston 70 out of the cylinder 46 draws air into the cylinder 46, and consequently the air tube 64, thereby reducing pressure at the probe tip 54. As mentioned above, the pressure release valve 40 is disposed within the air tube 64.

The piston 70 includes a cylinder end (not shown) within the pumping cylinder 46, and a linked end 72 outside of the pumping cylinder 46. The linked end 72 includes a passage that pivotally retains a link pin 74 that is supported by a lever arm 76. The lever arm 76 is pivotally supported to the base 66 through a pivot pin 78 distally located from the piston 70. The lever arm 76 is configured to pivot through a range of motion denoted by arcs B and B'.

The pump system 38 also includes the motor 44 operatively connected to an outwardly-extending threaded drive shaft 82. The motor 44 is configured to rotate the threaded drive shaft 82.

The threaded drive shaft 82 threadably engages a reciprocal threaded passage 84 of the lever arm 76. As shown in FIGS. 3-5, the threaded drive shaft 82 contacts the lever arm 76 only on a top surface 86 that defines a lower edge of the passage 84. That is, the passage 84 does not surround the drive shaft 82. Instead, the passage 84 is configured to threadably engage the drive shaft 82 at a minimum of points. For example, only a lower portion of the axial cross section of the drive shaft 82 contacts the top surface 86 of the passage 84. Because of this minimum contact, there is minimal friction between the drive shaft 82 and the lever arm 76. As such, minimal noise is produced when the drive shaft 82 rotates within the passage 84 of the lever arm 76, thereby minimizing audio interference from this interaction. The lever arm 76 may also be formed from a Teflon-doped plastic for minimum friction with the threaded drive shaft 82.

Additionally, the pump system 38 may include acoustic filters that filter or dampen the noise generated by the pump system 38. The filters may be acoustic dampers placed within transmission tubes, or acoustic low-pass filters provided in the transmission path.

As the drive shaft 82 is rotated by the motor 44, the threaded engagement between the drive shaft 82 and the passage 84 causes the lever arm 76 to pivot about the pivot pin 78. The drive shaft 82 and passage 84 are threaded such that when the upper surface 86 reaches an end of the threads of the drive shaft 82, continued rotation of the drive shaft 82 causes the lever arm to move in the opposite direction. For example, when the lever arm 76 reaches the end thread 88, continued rotation of the drive shaft 82 causes the lever arm 76 to move in the direction of arc B'. Conversely, when the lever arm reaches the end thread 90, continued rotation of the drive shaft 82 causes the lever arm 76 to move back in the direction of arc B.

Optionally, the threads of the drive shaft 82 and the passage 84 may be configured to allow movement of the lever arm 76 in one direction when the drive shaft 82 is rotated in a first direction. Barriers may be positioned proximate the end threads 88 and 90, thereby blocking further movement of the lever arm 76 even upon continued rotation of the drive shaft 82. The processing unit may then operate the motor 44 to reverse rotation of the drive shaft 82 in order to move the lever arm 76 in the opposite direction. For example, when the drive shaft 82 rotates to cause the lever arm 76 to come into contact with the negative pressure limit switch 92, the processing unit 61 may reverse the direction of the motor 80 to drive the piston 70 to create a positive pressure.

As the lever arm 76 pivots about the pivot pin 78, the piston 70 moves linearly in the directions of arrows A and A'. Because the piston 70 is pivotally connected to the lever arm 76 through the link pin 74, radial motion of the lever arm 76 causes linear motion of the piston 70. For example, radial motion of the lever arm 76 in the direction of arc B causes the piston 70 to move into the cylinder 46 in the direction of arrow A; while radial motion of the lever arm 76 in the direction of arc B' causes the piston 70 to move out of the cylinder 46 in the direction of arrow A'. As the piston 70 moves into the cylinder 46, air pressure increases within the air tube 64. As the piston moves out of the cylinder 46, air is drawn back into the cylinder 46, thereby decreasing air pressure within the air tube 64.

The lever arm 76 may only move over the threaded drive shaft 82 as far as the end threads 88 and 90. Further, movement of the piston 70 through the cylinder 46 is limited by the movement of the lever arm 76. The amount of positive and negative pressure produced by the pump system 38 is limited to the extent that the piston 70 moves through the cylinder 46. Maximum pressure (or maximum positive pressure) occurs when the lever arm 76 moves to the threaded end 88, while minimum pressure occurs (or maximum negative pressure) when the lever arm 76 moves to the threaded end 90. As the lever arm 76 moves away from the threaded end 88 back toward the threaded end 90 in the direction of arrow B', the piston 70, in turn, moves out of the cylinder 46 in the direction of arrow A', thereby decreasing the air pressure within the tube 64. Additionally, when the lever arm 76 moves away from the threaded end 90 toward the threaded end 88 in the direction of arrow B, the piston 70, in turn, moves into the cylinder 46 in the direction of arrow A, thereby increasing the air pressure within the tube 64. As such, the pump system 38 is a fixed displacement pump system that limits maximum and minimum pressures imparted to the air tube 46 (and therefore the probe 18).

The threaded drive shaft 82 may be threaded to accommodate particular maximum and minimum air pressures. For example, the length of the threaded area (from ends 88 to 90) determines the range of motion of the lever arm 76, and therefore the amount of maximum and minimum pressure imparted to the tube 64. Thus, the pump system 38 may be configured to produce maximum and minimum pressures that are well within safe ranges with respect to a human ear.

Additionally, the pump system 38 is more compact than prior tymp pump systems that include a motor connected to a peristaltic pump. In general, the pump system 38 may be a fraction of the length of a direct-drive pump design.

As shown in FIG. 5 in particular, the tymp module 14 also includes a positive pressure limit switch 92 and a negative pressure limit switch 94, which are in communication with the processing unit. The positive pressure limit switch 92 detects the farthest distance the lever arm 76 travels in the direction of arc B, while the negative pressure limit switch 94 detects the farthest distance the lever arm 76 travels in the direction of arc B'.

The center of motion of the lever arm 76 is the point at which zero positive and negative pressure is applied to the tube 64 (and therefore the probe tip 54, as shown in FIG. 1). That is, the center of motion of the lever arm 76 coincides with ambient air pressure. Movement of the lever arm 76 in the direction of arc B produces a positive pressure (with maximum positive pressure being applied when the lever arm 76 contacts the end thread 88), while movement of the lever arm 76 in the direction of arc B' produces a negative pressure (with maximum negative pressure, or minimum pressure being applied when the lever arm 76 contacts the end thread 90).

In order to apply appropriate pressures within the ear canal, the pump system 38 is calibrated to determine its center position. A determination of the center position, in turn, determines the point of ambient air pressure. However, the tymp system 14 may not be at its center position when the tymp system 14 is activated. Thus, the processing unit, such as processing unit 61 shown in FIG. 2, runs an initial calibration when the tymp system 14 is activated.

During the calibration, the motor 44 rotates the drive shaft 82, which in turn moves the lever arm 76. The positive pressure limit switch 92 senses the maximum range of motion of the lever arm 76 in the direction of arc B, while the negative pressure limit switch 94 senses the maximum range of motion of the lever arm 76 in the direction of arc B'. These sensed values are then analyzed by the processing unit, which computes the total range of motion of the lever arm 76 between the limit switches 92 and 94 and divides that range of motion by two to determine the center position, which coincides with ambient air pressure. Optionally, the processing unit may determine the amount of time between the lever arm 76 contacting, or coming closest, to the limit switches 92 and 94, divide the time by two, and place the lever arm 76 at the center position by using that time value.

After the lever arm 76, and therefore the piston 70, are centered, the pressure release valve 40 is opened and a reading is taken from the pressure sensor 42. The pressure reading at this point is then determined to be ambient air pressure, from which all other pressure changes are referenced. Because the ambient reading may vary due to barometric differences (e.g., altitude, weather, and the like), the "zero" or ambient pressure reading may be determined every time the tymp module 14 is powered on.

If it is determined that the probe 18 (shown in FIGS. 1 and 2) is within an ear canal of a patient (e.g., analyzing whether there is a change in pressure during the piston centering routine), the tymp module 14 may transmit an alert signal (such as a sound or flashing light) to remove the probe 18 from the ear canal. Alternatively, the pressure release valve 40 may be engaged at certain intervals during the centering process to limit the pressure applied to the ear canal.

The tymp module 14 may alternatively be calibrated while the probe 18 is within an ear canal of a patient. Initially, a tone may be applied within the ear canal through either of the sound receivers 36 and 52 (shown in FIG. 2). The tone is then monitored by the microphone 50 to determine an appropriate drive level for the test tone. The pump system 38 is then driven for a short, predetermined time. During this time, the tymp module 14, through the processing unit for example, measures the rate of change of pressure within the ear canal. The tymp module 14 then determines whether the rate of change of pressure corresponds to a normal rate of change of pressure in a reasonable sized ear canal (approximately 0.05 to 2 cc). If it does not, the tymp module 14 restarts. If the tymp module 14 determines that the ear canal is reasonably sized, the tymp module 14 uses the measured rate to determine an appropriate pump speed to use for testing so that the rate of change of pressure is consistent regardless of ear canal volume. The range of speed adjustment available in the pump system 38 may limit the minimum and maximum rate of pressure change.

The tymp module 14 may also be operated to analyze whether the pump system 38 is properly controlling air pressure within the probe. Initially, the tymp module 14 may control the pump system 38 to drive pressure in an ear canal to test levels, while analyzing pressure change rate to detect whether there is a leak, such as in the air tube 64. If an unacceptable pressure change rate is detected, signifying a possible leak, the lever arm 76 is re-centered.

Figure 6:
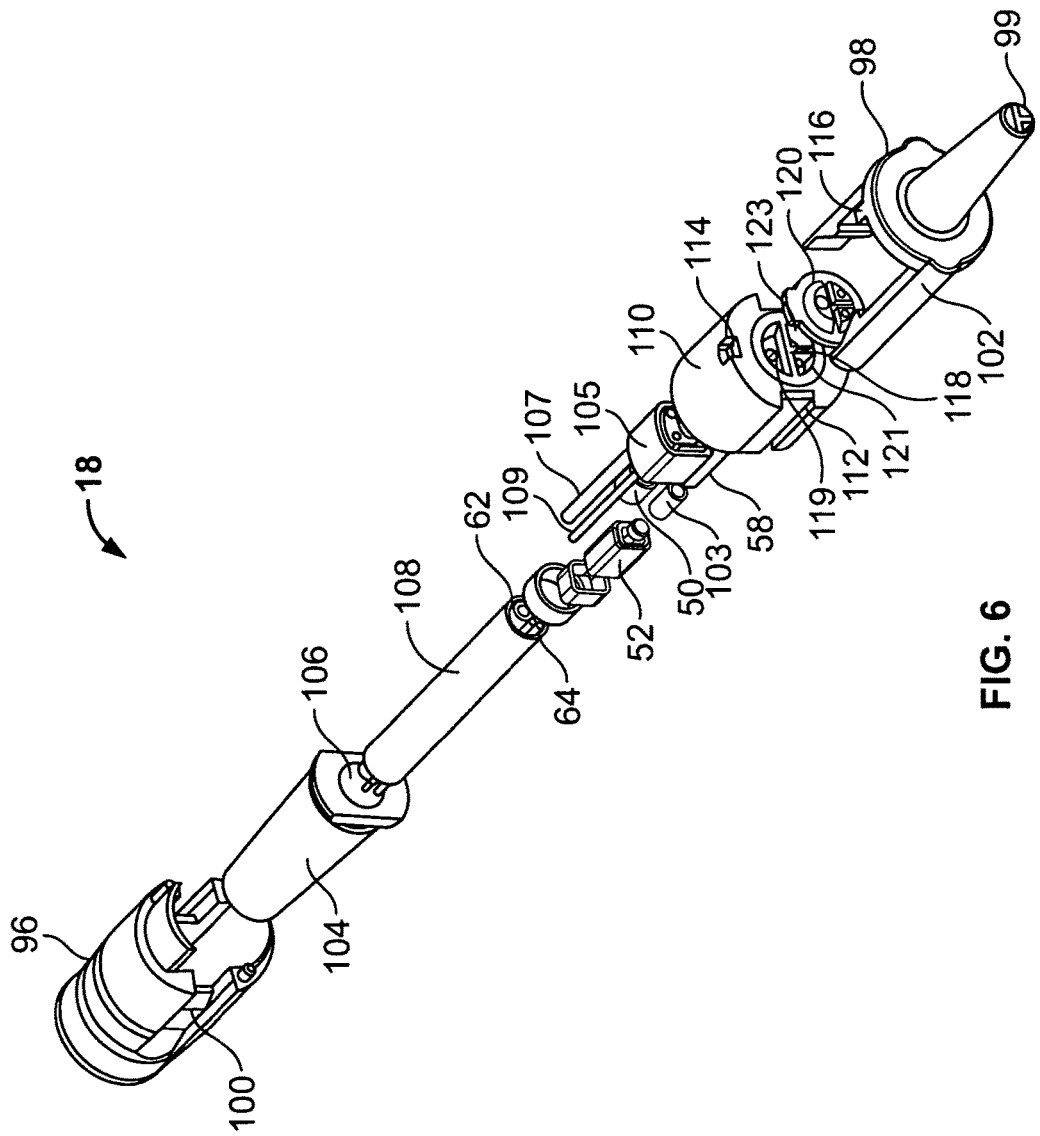
FIG. 6 illustrates an exploded view of a probe according to an embodiment of the present invention.

FIG. 6 illustrates an exploded view of the probe 18. The probe 18 includes a probe head including a rear probe housing 96, a front probe housing 110, and a probe tip 98 (such as the probe tip 54 shown in FIG. 2). The rear probe housing 96 includes channels 100 configured to receive and snapably retain lateral prongs 102 of the probe tip 98. The rear probe housing 96 is configured to snapably, latchably, or otherwise removably connect to the probe tip 98. The probe tip 98 also includes sound and air passages 99 formed therethrough.

A cable sheath 104 having a passage 106 formed therethrough is positioned within the rear probe housing 96. The cable sheath 104 protects against cable bending. A bundling cable 108 is positioned within the sheath 104 and is configured to securely bundle the air tube 64, the sensor tube 62, and the first sound tube 60 (hidden in FIG. 6) that connect to the interior components of the probe 18, as discussed above.

A microphone bracket 105, which retains the microphone 50, and the second sound receiver 52, including a coupling tube 103 that couples the second sound receiver 52 to the second sound tube 58, are securely retained within a front probe housing 110. Coupling tubes 107 and 109 extend outwardly from the rear of the microphone bracket 105 and couple the microphone bracket 105 to corresponding tubing in communication with the tymp module 14 (shown in FIGS. 1-5). The coupling tubes 107 and 109 receive and communicate with the air tube 64 (shown, e.g., in FIG. 2) and the sensor tube 62 (shown, e.g., in FIG. 2), respectively, by way of a press fit. The microphone 50 and the sound receiver 52 are connected to sound tubes, as discussed above. The front probe housing 110 includes lateral channels 112 and notches 114 configured to cooperate with the lateral prongs 102 and tabs 116, respectively, of the probe tip 98 in order to secure the front probe housing 110 within the probe tip 98. The front probe housing 110 includes a front face 118 having a microphone port 119, a second receiver port 121, and a first receiver port 123. A probe tip seal 120 may be positioned over the front face 118 of the front probe housing 110.

Figure 7:
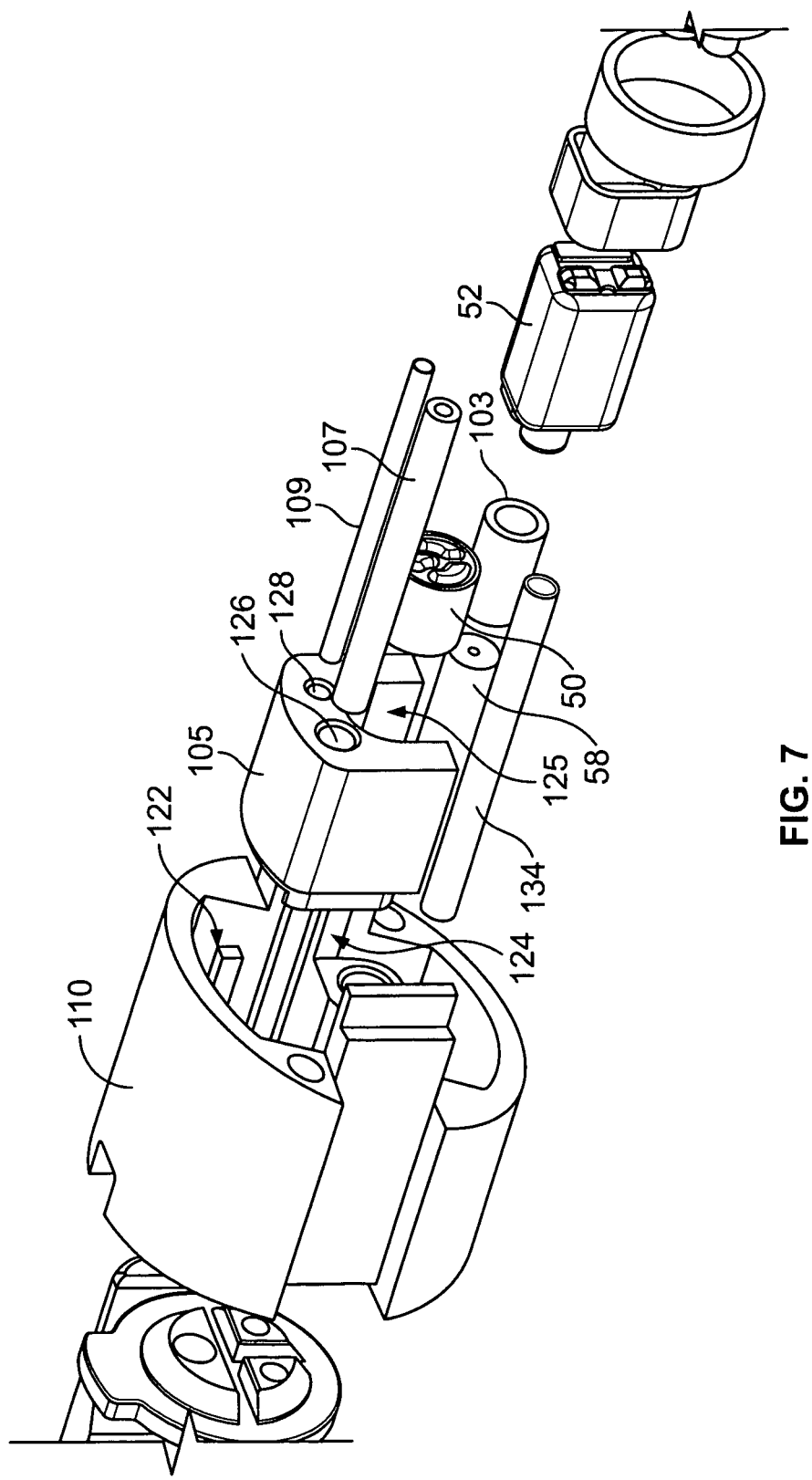
FIG. 7 illustrates an exploded rear view of components within a probe head of a probe according to an embodiment of the present invention.

FIG. 7 illustrates an exploded rear view of the components within the front probe housing 110. The front probe housing 110 includes a microphone housing passage 122 configured to receive and retain the microphone bracket 105. Additionally, the second sound receiver 52 is configured to be received and retained within a receiver passage 124 of the front probe housing 110. Tube 134, which may be an end of the first sound tube 60 (shown in FIG. 2) is received and retained within a reciprocal passage within the front probe housing 110.

The microphone bracket 105 includes a microphone channel 125 configured to receive and retain the microphone 50. Additionally, tube passages 126 and 128 are configured to receive coupling tubes 107 and 109, respectively.

Figure 8:
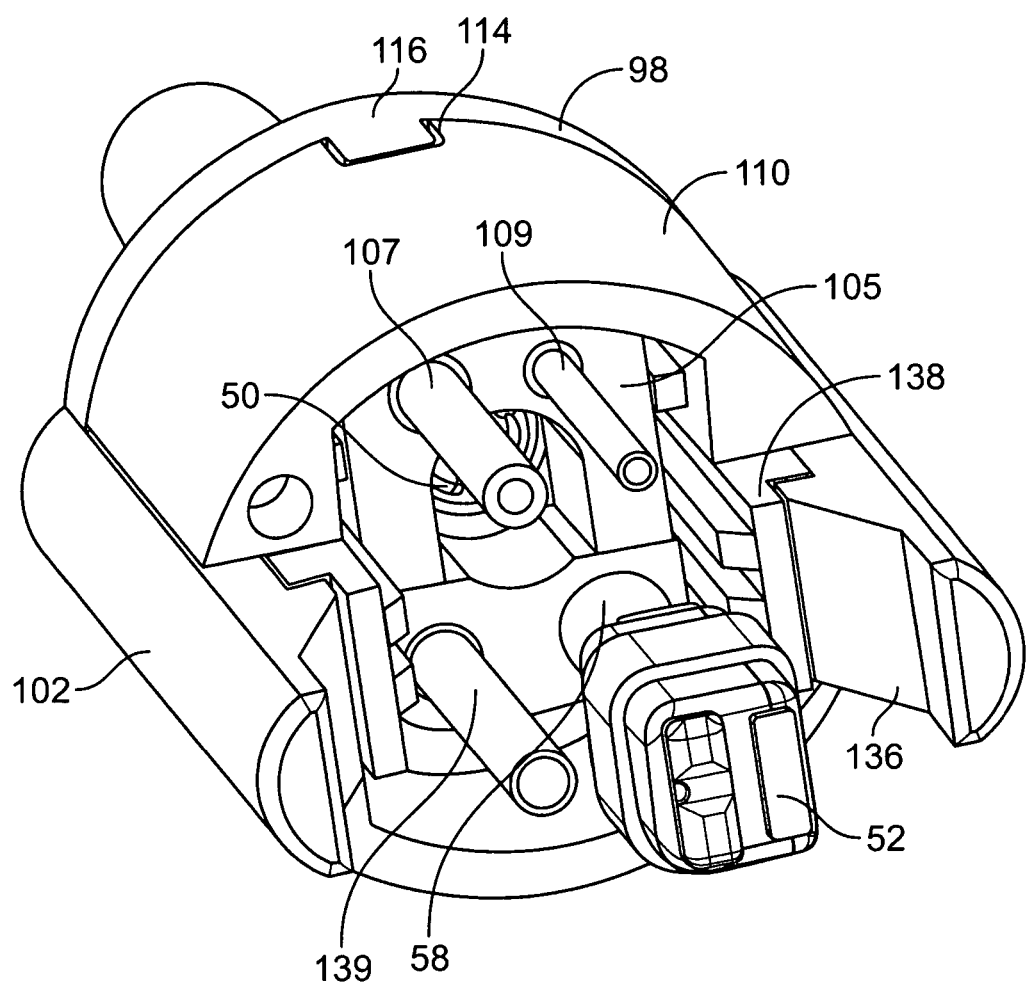
FIG. 8 illustrates an isometric rear view of a front probe housing coupled to a probe tip according to an embodiment of the present invention.

FIG. 8 illustrates an isometric rear view of the front probe housing 110 coupled to the probe tip 98. The lateral prongs 102 include snap members 136 that may snapably, latchably, or otherwise removably engage reciprocal members 138 of the front probe housing 110. Additionally, the tabs 116 of the probe tip 98 snapably mate with the notches 114 of the front probe housing 110.

Figure 9:
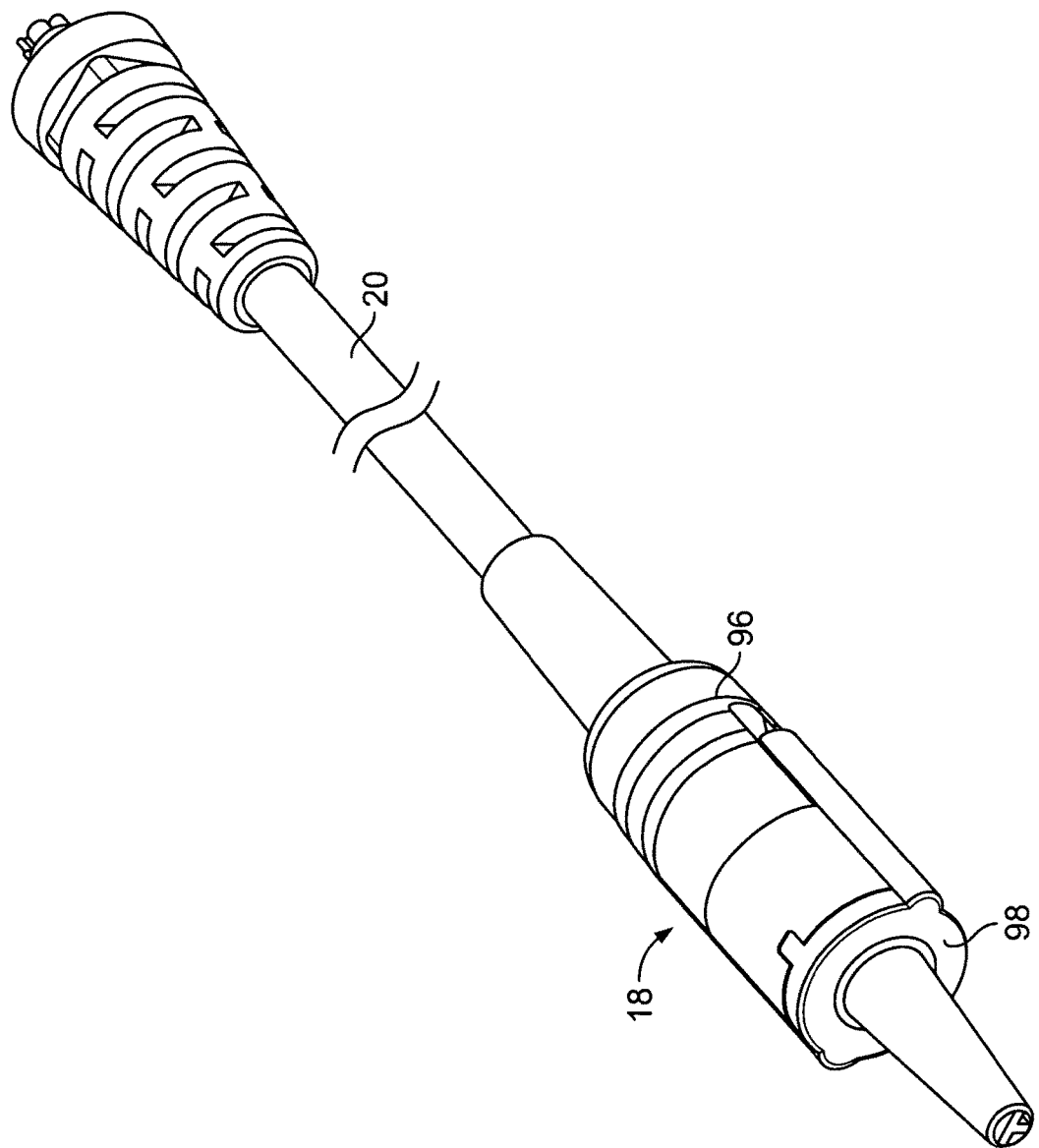
FIG. 9 illustrates an isometric view of a probe connected to a connection cable according to an embodiment of the present invention.

FIG. 9 illustrates an isometric view of the probe 18 connected to the connection cable 20. Once the probe tip 98 is mated with the rear probe housing 96 and the front probe housing 110, auditory and electrical signals may be passed from the probe 18 to the tymp module 14 (shown, for example, in FIGS. 1-5) and to the OAE module 12, which is connected to the probe 18 by way of the tymp module 14. Additionally, air pressure within the probe 18 may be varied through the tubing 64 (as shown, for example, in FIGS. 2 and 6-8).

Figure 10:
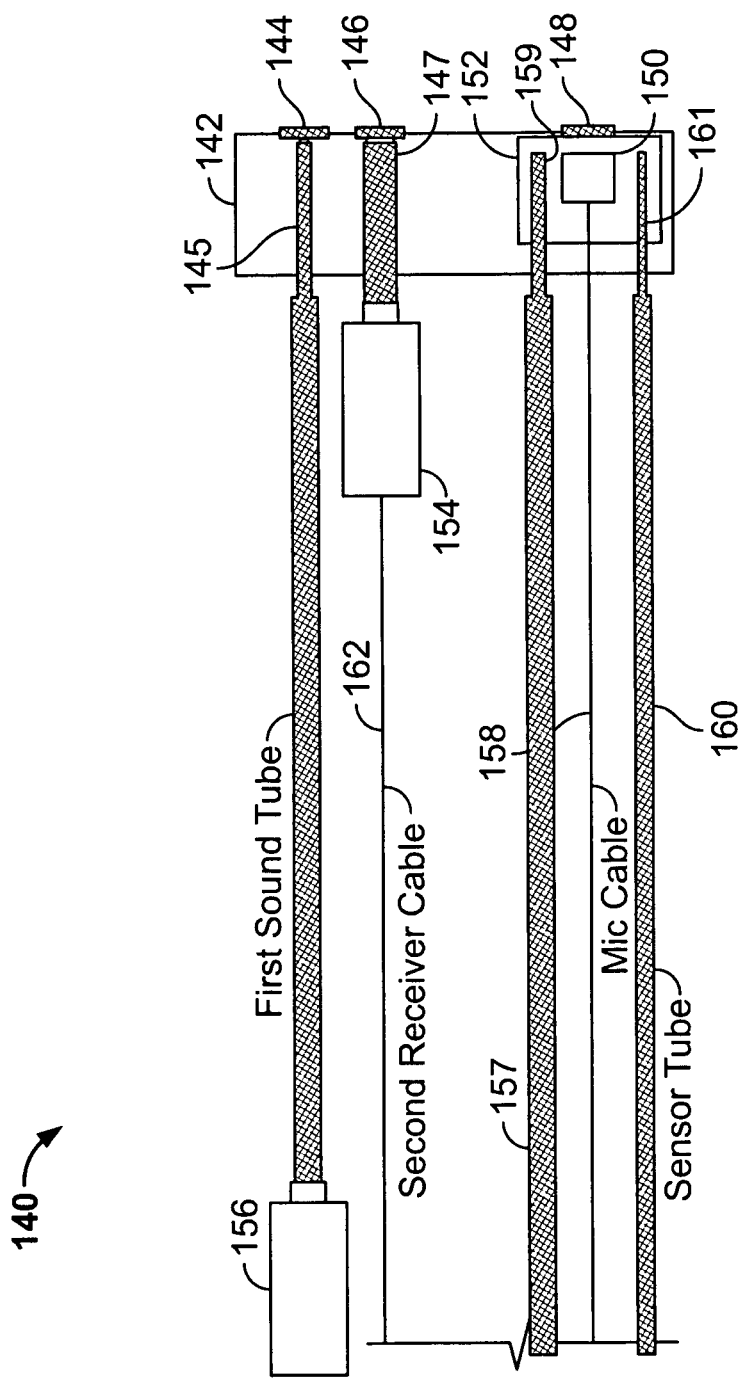
FIG. 10 illustrates a schematic diagram of a hearing screening system according to an embodiment of the present invention.

FIG. 10 illustrates a schematic diagram of a hearing screening system 140 according to an embodiment of the present invention. The hearing screening system 140 includes a probe 142 having a first receiver port 144 connected to a first sound tube 145, a second receiver port 146 connected to a second sound tube 147, a microphone port 148 in communication with a microphone 150 that is secured within the probe 142 through a microphone bracket 152, and a second sound receiver 154 secured within the probe 18.

A first sound receiver 156 is positioned out of the probe 18, and may be positioned within a tymp module, such as the tymp module 14, shown and described with respect to FIGS. 1-5. The first sound receiver 156 connects to the first receiver port 144 by way of the first sound tube 145. An air tube 157, a microphone cable 158, and a pressure sensor tube 160 may connect the microphone bracket 152 to the tymp module. Additionally, a second receiver cable 162 may connect the second sound receiver 154 to the tymp module 14 and/or the OAE module 12. As shown in FIG. 10, the air tube 157 may be in communication with a smaller diameter coupling tube 159 within the microphone bracket 152. Also, the sensor tube 160 may be in communication with a smaller diameter coupling tube 161 within the microphone bracket 152. The coupling tubes 159 and 161 may has inner diameters less than, for example, 0.6 mm.

As shown in FIG. 10, the portion of the first sound tube 145 (or coupling tube to which the first sound tube 145 is attached) within the probe 18 may have a smaller inner diameter than that of the sound tube 147 (or coupling tube to which the second tube 147 is attached). As such, the acoustic impedance of the first sound tube 145 may be higher than that of the second sound tube 147. Cross-talk between the tubes 145 and 147 is minimized due to the high acoustic impedance of the tube 145. Additionally, the air tube 157 and the sensor tube 160 have smaller diameters, and therefore higher acoustic impedances, than the second sound tube 147. While the diameters of the first sound tube 145, the air tube 156, and the sensor tube 160 vary, they may, optionally, be uniform throughout. Also, alternatively, the second sound tube 147 may have a smaller inner diameter than that of the first sound tube 145.

Figure 11:
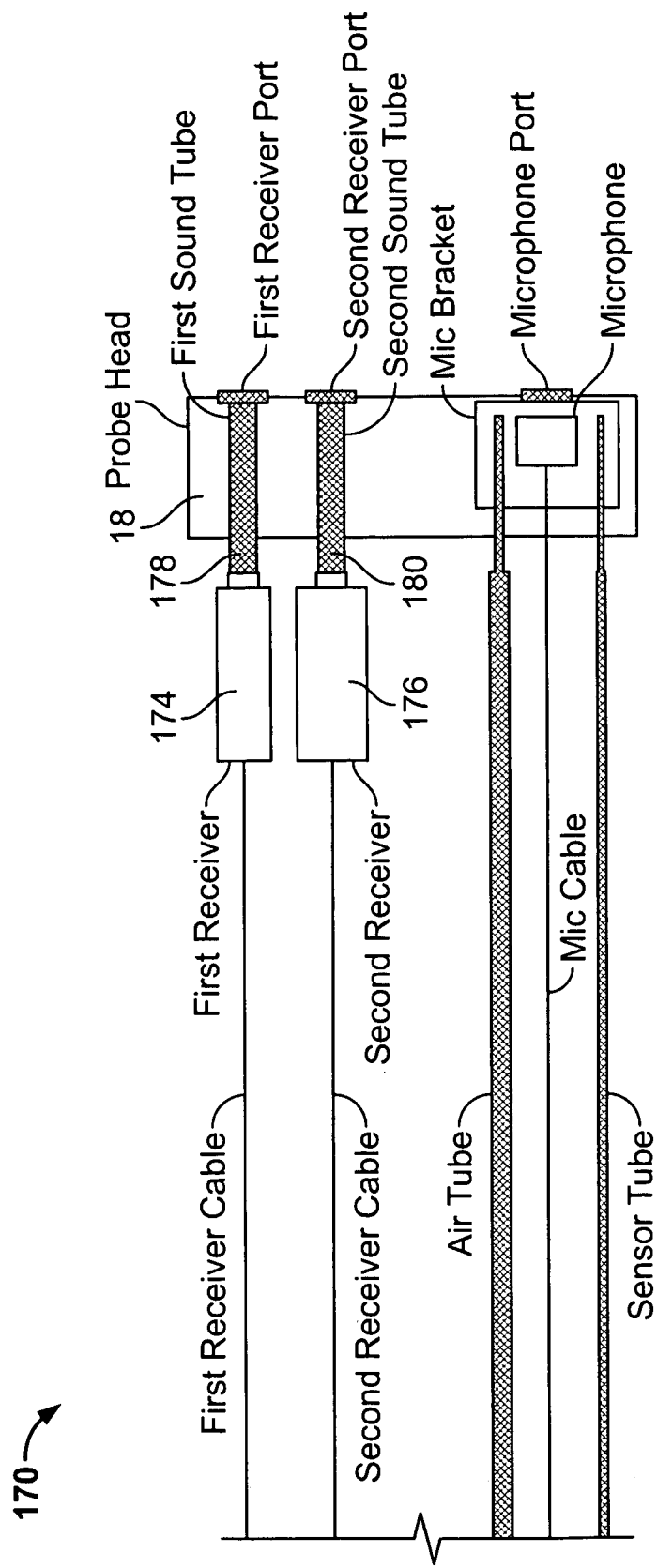
FIG. 11 illustrates a schematic diagram of a hearing screening system according to an embodiment of the present invention.

FIG. 11 illustrates a schematic diagram of a hearing screening system 170 according to an embodiment of the present invention. In this embodiment, a probe 172 includes first and second sound receivers 174 and 176 connected to sound tubes 178 and 180, respectively, each having short lengths and relatively small diameters. Alternatively, the diameters of the tubes 178 and 180 may be larger. The first and second receivers 174 and 176 may be oriented 90° with respect to one another so that their respective receiver diaphragms are not moving in the same plane.

Figure 12:
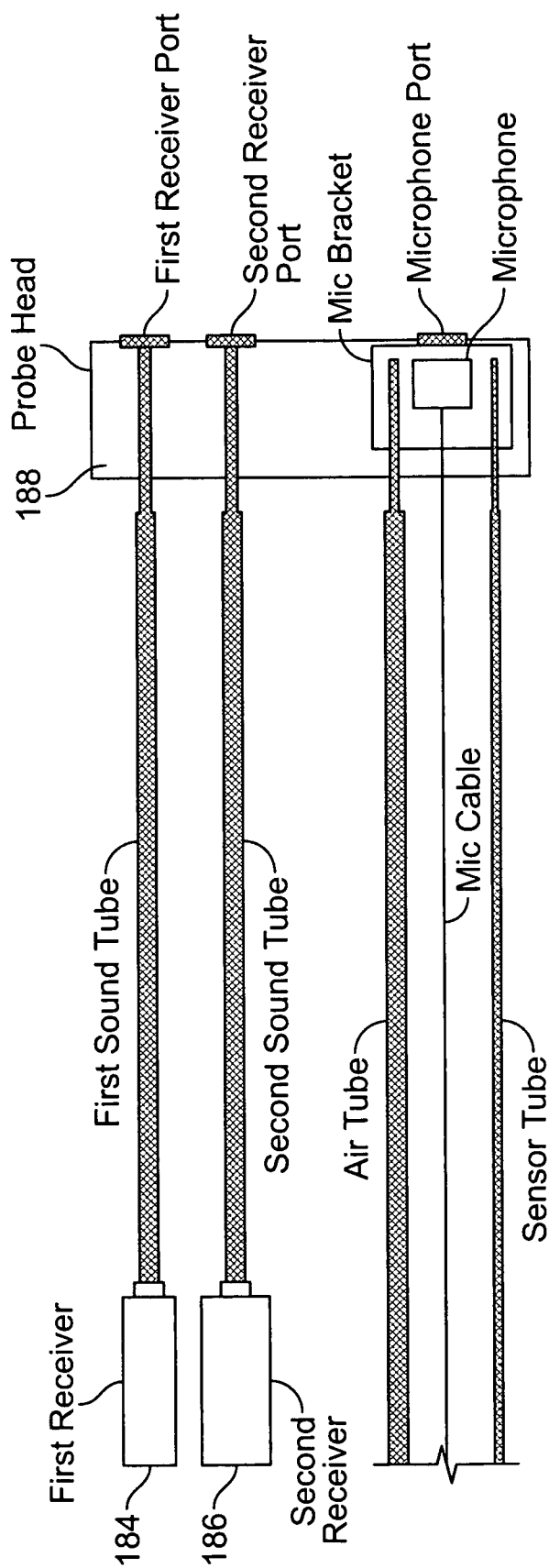
FIG. 12 illustrates a schematic diagram of a hearing screening system according to an embodiment of the present invention.

FIG. 12 illustrates a schematic diagram of a hearing screening system 182 according to an embodiment of the present invention. In this embodiment, the first and second sound receivers 184 and 186 are housed within a tymp module, instead of the probe 188.

Figure 13:
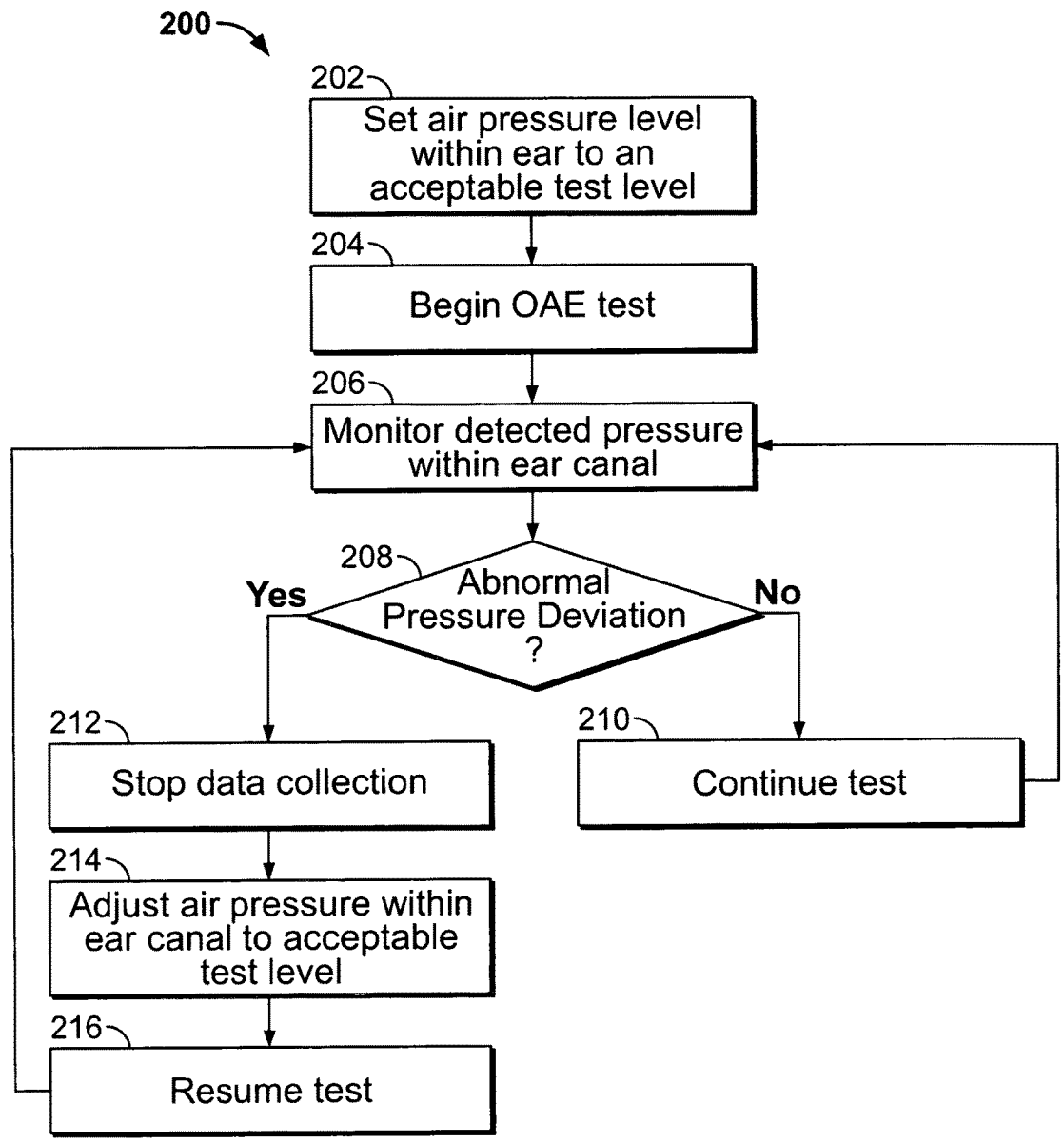
FIG. 13 illustrates a block diagram of an otoacoustic emission process, according to an embodiment of the present invention.

FIG. 13 illustrates a block diagram of a pressure-compensated otoacoustic emission (OAE) process 200, according to an embodiment of the present invention. In OAE testing, extraneous noises and sounds, such as those emanating from operation of a pump, may hinder proper testing. Therefore, at step 202, before the OAE test begins, a proper pressure within the ear canal is set, such as by the pump system 38 operating to provide a pressure within an ear canal via the probe 18. At step 204, the OAE test begins. At 206, the pressure sensor 42 continually detects the pressure within the ear canal, while the processing unit monitors the detected pressure. At 208, the processing unit determines whether there is an abnormal pressure deviation within the ear. If the pressure deviation is within a normal, acceptable range, the test continues at 210 and the process repeats at 206. If the pressure deviation is abnormal, data collection for the OAE test is halted at 212. The pressure within the ear canal is then adjusted to a normal test level at 214. The test then resumes at 216, and the process repeats at 206.

Figure 14:
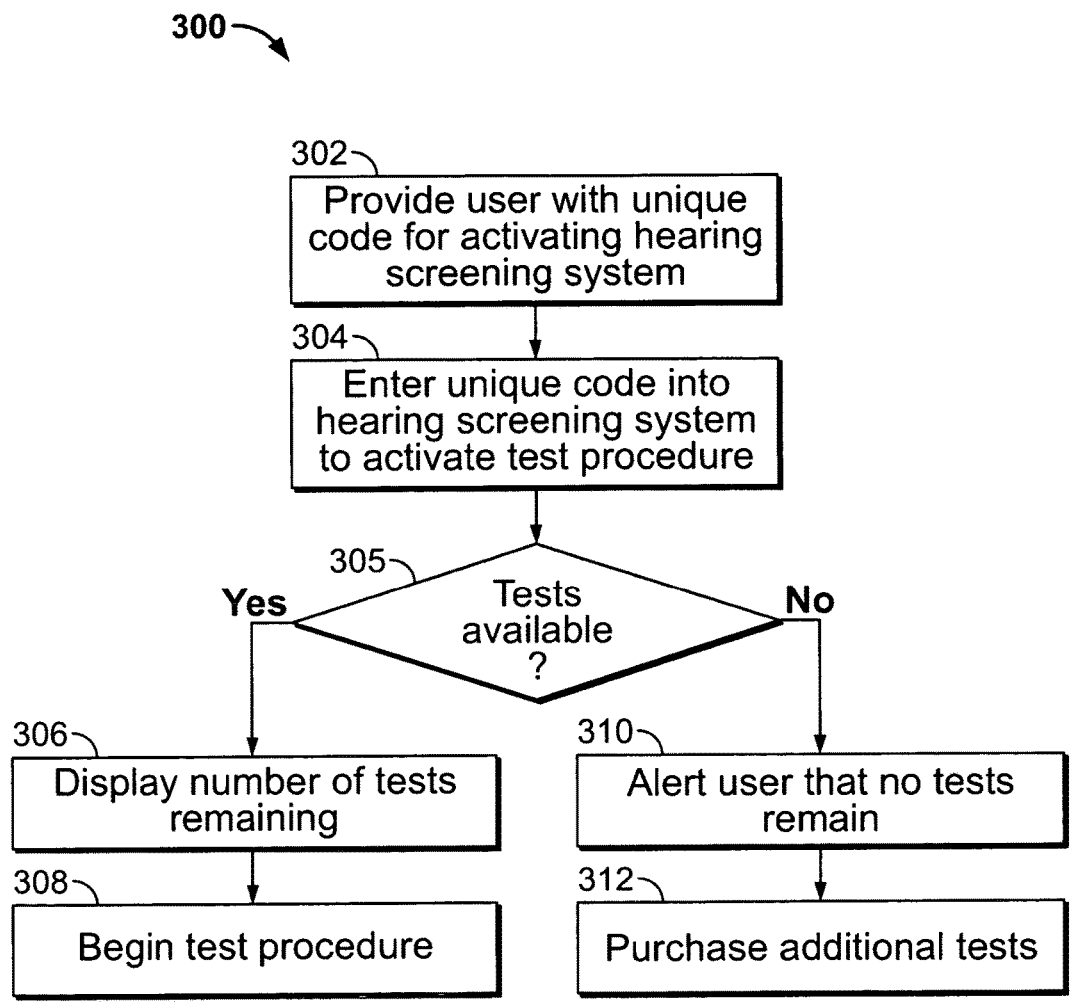
FIG. 14 illustrates a block diagram of a hearing screening activation method, according to embodiment of the present invention.

FIG. 14 illustrates a block diagram of a hearing screening activation method 300, according to embodiment of the present invention. A distributor of a hearing screening system (such as system 10) provides a user with a unique code for system activation at step 302. For example, if a user paid for fifty tests, the distributor provides a unique code to the user to enter into the system that will make fifty subsequent tests available.

The unique code may include an encrypted number based upon the serial number of the instrument, the current date, and the number of tests to be provided. The code may be encrypted by a program maintained by the distributor and may be decoded by an algorithm contained in the firmware of the instrument. When the code is entered and verified by the instrument, the purchased number of tests become available for use. The verified key is then stored in the memory of the instrument and may not be used again.

Alternatively, the unique code relates to a matching code stored in a memory of the system. The unique code may correspond to a particular number of tests. For example, the system may have stored fifty matching codes that relate to activation commands for fifty pre-paid tests. The fifty activation commands are activated by a user inputting the unique code into the system. The system may only recognize the unique code for a number of pre-paid tests. For example, after the user enters the unique code into the system a first time, the system will allow the user to perform a test. However, the system also tracks that the unique code was used, and that only forty-nine tests remain related to the unique code. Optionally, the system may have fifty matching activation codes. Each time a user enters the unique code into the system for test activation, one matching activation code is deleted from the memory. When all matching codes are deleted from memory, the system will no longer recognize the unique code. As such, a user may not use a unique code that relates to a stored number of activation codes more than the number of tests for which the user paid.

At step 304, a user enters the unique code into the hearing screening system, such as through a keypad, to begin a hearing test. The system determines whether any pre-paid tests remain at 305. If there are remaining activation codes stored in the system, at 306, the system displays the number of remaining tests left that correspond to the user's activation code. The user may then begin a hearing test using the system at 308. If no activation codes remain stored in the system, at 310, the system alerts the user, such as through a text message on a display, that no tests remain that correspond to the input unique code. At 312, the user may contact the distributor and purchase additional tests corresponding to a different unique code. For example, the distributor may provide a unique code that corresponds to fifty additional tests. Each system may also be operable to recognize a system test code, that allows the system itself to be tested and/or calibrated without depleting a stored test activation.

Thus, embodiments provide a safe, compact system and method for performing OAE and tympanometry screening. Embodiments of the present invention allow for various hearing tests to be performed without changing any hardware. For example, the OAE module may perform OAE tests and procedures, while the tymp module may perform tympanometry tests and procedures. In tympanometry tests, the system utilizes the air tube and the microphone within the probe head, along with the first and/or second receivers. In OAE tests, the system utilizes the first and second receivers along with the microphone within the probe head.

Also, because the sound tubes have different sizes, and therefore acoustic impedances, cross-talk may be minimized between the sound tubes. Thus, distortion product tests may be performed because the independent lines do not interfere with one another. In general, embodiments of the present invention provide a single system that may utilize tympanometry and acoustic reflexes; evoked responses, such as otoacoustic emission measures and auditory brainstem response; and behavioral responses, such as pure-tone testing.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

The invention claimed is:

1. A hearing screening system for testing hearing abilities of a patient, comprising:
   an otoacoustic emission (OAE) module operable to perform OAE tests using a probe;
   a tympanometry (tymp) module operable to perform tymp tests using said probe; and
   said probe in communication with said OAE module and said tymp module, said probe having a probe tip being configured to be positioned within an ear canal of the patient,
   wherein said tymp module comprises: (i) a pressure sensor in direct communication with said probe through a sensor tube, wherein said pressure sensor is configured to detect air pressure proximate said probe tip via said sensor tube; and (ii) a pump subsystem directly connected to said probe through an air tube, wherein an entire length of said air tube is separate and distinct from an entire length of said sensor tube, and wherein said pump subsystem is operable to vary air pressure proximate said probe tip via said air tube.

2. The hearing screening system of claim 1, wherein said OAE module comprises a handheld device, and wherein said tymp module comprises a separate housing connected to said handheld device.

3. The hearing screening system of claim 1, wherein said OAE module and said tymp module are contained within a handheld device.

4. The hearing screening system of claim 1, wherein said pump subsystem is a fixed displacement pump subsystem that limits applied maximum and minimum air pressure.

5. The hearing screening system of claim 1, wherein said pump subsystem comprises:
   a pump cylinder in fluid communication with said air tube;
   a piston slidably retained within said pump cylinder;
   a link pivotally connected to said pump cylinder; and
   a lever arm supporting said link, wherein radial motion of said lever arm is translated into linear motion of said piston within said pump cylinder through said link.

6. The hearing screening system of claim 5, further comprising first and second limit switches operable to detect a position of said lever arm.

7. The hearing screening system of claim 5, further comprising a motor operatively connected to a drive shaft that engages said lever arm, wherein said motor is operable to rotate said drive shaft, and wherein the rotation of said drive shaft causes said lever arm to radially move.

8. The hearing screening system of claim 7, wherein said drive shaft is threaded from a first location to a second location, wherein said drive shaft threadably engages said lever arm, and wherein movement of said lever arm on said drive shaft is limited between movement from said first location to said second location.

9. The hearing screening system of claim 1, further comprising a pressure relief valve disposed within said air tube between said pump subsystem and said probe.

10. The hearing screening system of claim 1, wherein said probe comprises at least one sound receiver and a microphone.

11. The hearing screening system of claim 1, wherein said tymp module comprises a first sound receiver in communication with said probe through a first sound tube having a first inner diameter, wherein said probe comprises a second sound receiver connected to a second sound tube having a second inner diameter, and wherein said first and second inner diameters differ.

12. The hearing screening system of claim 1, further comprising a user interface and a memory storing a plurality of activation codes corresponding to pre-paid hearing tests, wherein a test procedure is activated when a unique code input at said user interface matches one of said plurality of activation codes.

13. A tympanometry (tymp) system for testing hearing of a patient, the tymp system comprising:
   a probe having a probe tip configured to be positioned within an ear canal of the patient;
   an air pressure sensor operatively connected to said probe through a sensor tube, wherein said air pressure sensor is configured to detect air pressure proximate said probe tip;
   a pump subsystem operatively connected to said probe through an air tube, wherein said pump subsystem is operable to vary air pressure proximate said probe; and
   a first sound receiver in communication with said probe through a first sound tube having a first inner diameter, wherein said probe comprises a second sound receiver connected to a second sound tube having a second inner diameter, and wherein said first and second inner diameters differ,
   wherein an entire length of said connection between said air pressure sensor and said probe is separate and distinct from an entire length of said connection between said pump subsystem and said probe.

14. The tymp system of claim 13, further comprising a pressure relief valve disposed within said air tube between said pump subsystem and said probe.

15. A probe having a probe tip configured to be positioned within an ear canal of a patient during a hearing test, the probe comprising:
   a rear housing;
   a probe tip configured to removably secure to said rear housing, said probe tip configured to be positioned within the ear canal of the patient;
   a probe head securely retained within at least one of said rear housing and said probe tip, said probe head having a microphone port, a first sound receiver port and a second sound receiver port;
   a microphone secured within said probe head proximate said microphone port;
   a first sound receiver secured within said probe head, said first sound receiver coupling to said first sound receiver port through a first sound tube;

an air tube operable to provide air pressure to the ear canal of the patient, said air tube disposed within at least one of said rear housing and said probe tip; and an air pressure sensor tube, separate and distinct from said air tube, operable to receive air pressure proximate said probe tip, said air pressure sensor tube disposed within at least one of said rear housing and said probe tip, wherein an entire air pressure path of said air pressure sensor tube and an entire air pressure path of said air tube are independent of each other.

16. The probe of claim 15, further comprising a second sound tube connected to said second sound receiver port.

17. The probe of claim 16, wherein an inner diameter of said first sound tube differs from an inner diameter of said second sound tube.

18. The probe of claim 15, further comprising a second sound receiver secured within said probe head, said second sound receiver coupling to said second sound receiver port through a second sound tube.

\* \* \* \* \*